United States Patent [19]

Farooq et al.

[11] Patent Number: 4,812,464
[45] Date of Patent: Mar. 14, 1989

[54] PESTICIDAL 2-PYRIDYL-4,5-DIHYDRO-1,3,4-THIADIAZOLES

[75] Inventors: Saleem Farooq, Arisdorf; Josef Ehrenfreund; Hans-Rudolf Waespe, both of Allschwil, all of Switzerland

[73] Assignee: Ciba-Geigy Corporation, Ardsley, N.Y.

[21] Appl. No.: 129,199

[22] Filed: Dec. 7, 1987

[30] Foreign Application Priority Data

Dec. 18, 1986 [CH] Switzerland .................. 5059/86

[51] Int. Cl.$^4$ .................. C07D 401/00; C07D 405/00; A01N 43/48
[52] U.S. Cl. .................. 514/333; 546/256; 546/277; 514/342
[58] Field of Search .................. 546/256, 277; 514/333, 514/342

[56] References Cited

U.S. PATENT DOCUMENTS 4,692,456 9/1987 Ife ........................ 546/256
4,699,913 10/1987 Farooq et al. .......... 546/256

OTHER PUBLICATIONS

J. Chem. Soc., Perkin Trans. 1 (1981).
J. Chem. Soc., Chem. Commun., p. 188 (1982).
Khimiya Geterotsiklicheskikh Soedinenii, No. 7, pp. 904–910 (1982), (translated).

Primary Examiner—Mary C. Lee
Assistant Examiner—Robert C. Whittenbaugh
Attorney, Agent, or Firm—Kevin T. Mansfield; Edward McC. Roberts

[57] ABSTRACT

The invention relates to novel 2-pyridyl-4,5-dihydro-1,3,4-thiadiazoles of formula

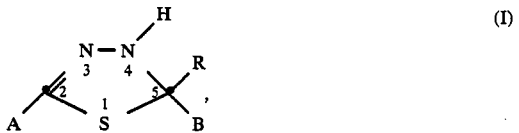

wherein
A is the 2-, 3- or 4-pyridyl radical,
B is hydrogen, $C_1$–$C_4$alkyl or the 2-, 3- or 4-pyridyl radical,
R is hydrogen, $C_1$–$C_4$alkyl, benzyl, aryl or aryl which is substituted by halogen, nitro, $C_1$–$C_4$alkyl, $C_1$–$C_4$alkoxy, $C_1$–$C_4$alkoxy-$C_1$–$C_4$alkyl or halo-$C_1$–$C_4$alkyl.

The invention further relates to the preparation of these novel compounds and to the use thereof in pest control.

11 Claims, No Drawings

PESTICIDAL 2-PYRIDYL-4,5-DIHYDRO-1,3,4-THIADIAZOLES

The present invention relates to novel unsubstituted or substituted 2-pyridyl-4,5-dihydro-1,3,4-thiadiazoles, to their preparation, and to the use thereof in pest control, as well as to compositions which contain these compounds.

Specifically, the invention relates to novel 2-pyridyl-4,5-dihydro-1,3,4-thiadiazoles of formula I

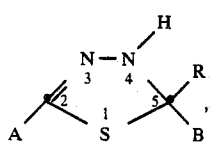

wherein
A is the 2-, 3- or 4-pyridyl radical,
B is hydrogen, $C_1$-$C_4$alkyl or the 2, 3- or 4-pyridyl radical,
R is hydrogen, $C_1$-$C_4$alkyl, benzyl, aryl or aryl which is substituted by halogen, nitro, $C_1$-$C_4$alkyl, $C_1$-$C_4$alkoxy, $C_1$-$C_4$alkoxy-$C_1$-$C_4$alkyl or halo-$C_1$-$C_4$alkyl,
and to salts and optical isomers thereof.

$C_1$-$C_4$Alkyl groups R by themselves or as moieties of other radicals may be branched or straight chain. Such alkyl groups are typically methyl, ethyl, and propyl, butyl and the isomers thereof.

Aryl groups R are mononuclear or polynuclear radicals, preferably unsubstituted and substituted phenyl radicals and 1- or 2-naphthyl radicals.

R as halogen is fluorine and chlorine as well as bromine and iodine. R is preferably fluorine and chlorine. This definition of halogen also applies to $C_1$-$C_4$haloalkyl and haloaryl groups. Typical haloalkyl groups are methyl which is substituted by 1 to 3 fluorine, chlorine and/or bromine atoms, ethyl which is substituted by 1 to 5 fluorine, chlorine and/or bromine atoms, or propyl which is substituted by 1 to 7 fluorine, chlorine and/or bromine atoms. Haloaryl groups are typically phenyl radicals which are substituted by 1 to 3 fluorine, chlorine and/or bromine atoms.

The present invention also relates to the salts, in particular the phytophysiologically acceptable salts, of the compounds of formula I. Examples of such salts with organic and inorganic acids are: chlorides, bromides, iodides, sulfates, bisulfates, chlorates, perchlorates, rhodanides, nitrates, phosphates, hydrogen phosphates, tetrafluoroborates, formates, acetates, trichloroacetates, trifluoroacetates, phenylsulfonates, oxalates, malonates, succinates, malates, tartrates or citrates. Preferred salts are the bromides.

The present invention also relates to the optical isomers of the compounds of formula I which can be obtained from the racemic forms in a manner known per se by conventional separation methods.

Preferred compounds of formula I are those wherein B is the 2-, 3- or 4-pyridyl radical and R is hydrogen or $C_1$-$C_4$alkyl.

Among these compounds, those compounds are especially preferred in which A is the 3-pyridyl radical and R is hydrogen.

Among this group of compounds, 2,5-bis(3-pyridyl)-4,5-dihydro-1,3,4-thiadiazole and the salts thereof merit special interest.

Interesting compounds of formula I are also those in which B is the 2-, 3- or 4-pyridyl radical, R is hydrogen and A is the 2- or 4-pyridyl radical.

Further interesting compounds of formula I are those in which A is the 3- or 4-pyridyl radical, B is hydrogen and R is phenyl or phenyl which is monosubstituted by halogen, ethyl or trifluoromethyl.

Among this group of compounds, those compounds merit particular interest in which A is the 3-pyridyl radical and R is the radical

Among these halogenated compounds, the preferred individual compound is 2-(3-pyridyl)-5-(4-chlorophenyl)-4,5-dihydro-1,3,4-thiadiazole.

The compounds of formula I can be prepared in a manner known per se (q.v. D. M. Evans et al., J. Chem. Soc., Chem. Commun. 1982, p. 188; K. N. Zelenin et al., Khim. Geterotsikl. Soedin, 1982 (No. 7), p. 904) by reacting a compound of formula II

with a compound of formula III

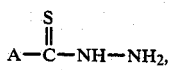

in which compounds of formulae II and III A, B and R are as defined above for formula I [process a)].

The compounds of formula I can also be prepared by reacting a compound of formula IV

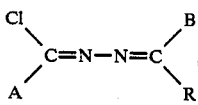

wherein A, B and R are as defined for formula I, with a sulfide (process b). The compounds of formula IV can be prepared by methods analogous to known ones (q.v. J. Chem. Soc., Perkin Trans., 1 (2), 349-55; 1981).

If desired, a compound of formula I obtained as described above can be converted in a manner known per se into a salt thereof.

Process (a) yielding compounds of formula I is preferably carried out in a solvent. Examples of suitable solvents are aromatic hydrocarbons such as benzene, toluene and xylene; ketones such as acetone, cyclohexanone and methyl ethyl ketone; ethers such as tetrahydrofuran, dioxane and diethyl ether; halogenated hydrocarbons such as chloroform, carbon tetrachloride and chlorobenzene; alcohols such as ethanol and propanol; esters of aliphatic acids such as ethyl acetate; aliphatic amides such as dimethylformamide and dimethylacetamide; dimethyl sulfoxide and other solvents which do not impair the reaction. Mixtures of these solvents may also be employed. The reaction temperatures may be in a wide range from −10° to +200° C. A temperature range from room temperature to about 150° C. is preferred.

Process (b) is preferably carried out in a polar solvent such as water, or an alcohol, e.g. methanol or ethanol. The cyclisation is effected with a sulfide, preferably a soluble metal sulfide such as sodium sulfide or potassium sulfide, or a corresponding hydrogen sulfide, preferably in an alkaline medium. The reaction temperature may be in the range from −15° to +100° C. A temperature in the range from −10° to +50° C., e.g. room temperature, is preferred.

The starting carbonyl compounds of formula II and the pyridinethiocarboxylic acid hydrazides of formula III are known or can be obtained by processes analogous to known ones. The substituted 2,3-diazabutadienes of formula IV can be obtained by procedures analogous to known ones (q.v. J. Chem. Soc., Perkin, Trans., 1 (2), p. 349, 1981) as follows, in which formulae $R_1$ and $R_2$ are as defined above;

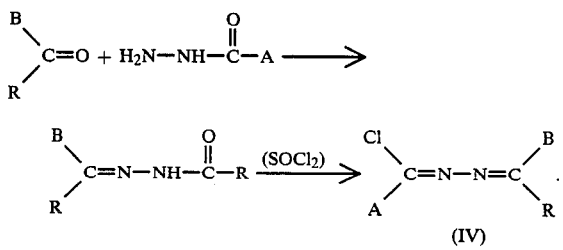

Among the substituted butadienes of formula IV, those of formula IVa

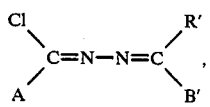

wherein A and B' are each independently of the other the 2-, 3- or 4-pyridyl radical and R' is hyrogen or $C_1$-$C_4$alkyl, are novel. The compounds of formula IVa likewise constitute an object of the present invention.

It has been found that the compounds of formula I exhibit excellent activity as pesticides, while being well tolerated by plants and having low mammalian toxicity to warm-blooded animals. The compounds of formula I are particularly suitable for controlling pests that attack plants and animals.

In particular, the compounds of formulae I and Ia are suitable for controlling insects of the orders: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera, as well as representatives of the order Acarina.

The good pesticidal activity of the compounds of the invention corresponds to a mortality of at least 50-60% of the above pests.

Most particularly plant-destructive insects, especially plant-destructive insects in ornamentals and crops of useful plants, in particular in cotton, vegetable, rice and fruit crops, can be controlled with the compounds of formula I. In this connection, particular attention is drawn to the fact that the compounds of formula I have a strongly pronounced systemic as well as contact action against sucking insects, especially against insects of the Aphididae family (e.g. against *Aphis fabae, Aphis craccivora* and *Myzus persicae*), which can only be controlled with difficulty using known pesticides.

The compounds of formula I also exhibit good activity against larval insect stages and nymphs, especially of noxious feeding insects. In particular, the compounds of formula 1 can be used with great success against plant-destructive cicadas, especially in rice crops.

The compounds of formula I are also suitable for controlling ectoparasites, e.g. *Lucilia sericata,* and ticks on domestic animals and productive livestock, e.g. by treating animals, barns, stables etc., and pastures.

The activity of the compounds of formula I and of the compositions containing them can be substantially broadened and adapted to prevailing circumstances by addition of other insecticides and/or acaricides. Examples of suitable additives include: organophosphorus compounds, nitrophenols and derivatives thereof, formamidines, ureas, carbamates, pyrethroids, chlorinated hydrocarbons, and Bacillus thuringiensis preparations.

The compounds of formula I are used in unmodified form, or preferably together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the nature of the compositions, the methods of application such as spraying, atomising, dusting, scattering or pouring, are chosen in accordance with the intended objectives and the prevailing circumstances.

The formulations, i.e. the compositions, preparations or mixtures containing the compound (active ingredient) of formula I or combinations thereof with other insecticides or acaricides, and, where appropriate, a solid or liquid adjuvant, are prepared in known manner, e.g. by homogeneously mixing and/or grinding the active ingredients with extenders, e.g. solvents, solid carriers and, in some cases, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed and absorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverised plant residues.

Depending on the nature of the compound of formula I to be formulated, or of combinations thereof with other insecticides or acaricides, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained, e.g. from coconut oil or tallow oil. Further suitable surfactants are also the fatty acid methyltaurin salts as well as modified and unmodified phospholipids.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and generally contain a $C_8$–$C_{22}$alkyl radical which also includes the alkyl moiety of acyl radicals, e.g. the sodium or calcium salt of lignosulfonic acid, of dodecylsulfate, or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing about 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polygylcol ethers, castor oil thioxilate, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxylower alkyl radicals. The salts are preferably in the form of halides, methylsulfates or ethylsulfates, e.g. stearyltrimethylammonium chloride or benzyldi-(2-chloroethyl)ethylammonium bromide.

The surfactants customarily employed in the art of formulation are described e.g. in "McCutcheon's Detergents and Emulsifiers Annual", MC Publishing Corp., Ridgewood, N.J., 1979; Dr. Helmut Stache, "Tensid Taschenbuch" (Handbook of Surfactants), Carl Hanser Verlag, Munich/Vienna, 1981.

The pesticidal compositions usually contain 0.1 to 99%, preferably 0.1 to 95%, of a compound of formula I or combinations thereof with other insecticides or acaricides, 1 to 99.9% of a solid or liquid adjuvant, and 0 to 25%, preferably 0.1 to 20%, of a surfactant.

Whereas commercial products are preferably formulated as concentrates, the end user will normally employ diluted formulations of substantially lower concentration.

The compositions may also contain further ingredients, such as stabilisers, antifoams, viscosity regulators, binders, tackifiers as well as fertilisers or other active ingredients for obtaining special effects.

PREPARATORY EXAMPLES

Example P1

Preparation of 3-pyridinecarbonylpyridine-3-aldehyde hydrazone

Five drops of glacial acetic acid are added at room temperature to a solution of 41.1 g (0.3 mole) of nicotinyl hydrazide and 32.1 g (0.3 mole) of pyridine-3-aldehyde in 300 ml of ethanol. The product precipitates from the reaction mixture after 2 hours and is isolated by filtration, washed with 100 ml of ethanol and dried, to give 3-pyridinecarbonylpyridine-3-aldehyde hydrazone of formula

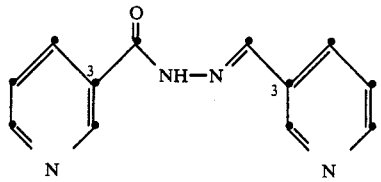

with a melting point of 213°–216° C.

Example P2

Preparation of 1-chloro-1,4-bis(pyrid-3-yl)-2,3-diazabutadiene (compound 4.1)

A suspension of 60.2 g (0.266 mole) of 3-pyridinecarbonylpyridine-3-aldehyde hydrazone is reacted in 1100 ml of boiling toluene with 94.9 g (0.789 mole) of thionyl chloride. The solvent is removed under vacuum after boiling for c. 8 hours, the residue is dissolved in 700 ml of tetrahydrofuran, and the solution is stirred in 41 g of triethylamine. The solvent is removed by evaporation under vacuum after stirring for 30 minutes at room temperature, and the residue is dissolved in ethyl acetate. The solution is washed with water and with a saturated solution of sodium chloride, dried over $Na_2SO_4$, and the solvent is removed by evaporation. The residue is triturated with hot tetrahydrofuran and the product is isolated by filtration and dried, to give 1-chloro-1,4-bis(pyrid-3-yl)-2,3-diazabutadiene of formula

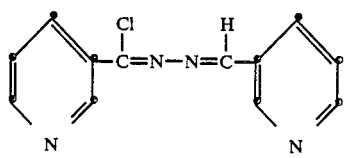

with a melting point of 103°–105° C.

Example P3

Preparation of 2,5-bis(pyrid-3-yl)-4,5-dihydro-1,3,4-thiadiazole (compound 1.1)

To a solution of 6.7 g (0.1 mole) of 85% potassium hydroxide in 190 ml of ethanol which has been freshly saturated with hydrogen sulfide are added 24.3 g (0.1 mole) of 1-chloro-1,4-bis(pyrid-3-yl)-2,3-diazabutadiene at low temperature. After 2 hours the solvent is removed by evaporation under vacuum and the residue is dissolved in ethyl acetate. The ethyl acetate solution is washed with water and with a saturated solution of sodium chloride, then dried over sodium sulfate, filtered, and the filtrate is concentrated by evaporation. The residue is stirred in hexane/ether, filtered, washed and dried, affording 2,5-bis(pyrid-3-yl)-4,5-dihydro-1,3,4-thiadiazole of formula

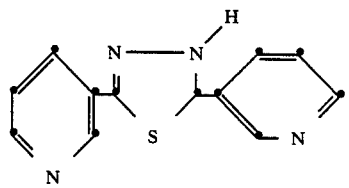

with a melting point of 77°–78° C.

Example P4

(a) Preparation of 1-nicotinoyl-2-(4-chlorobenzylidene) hydrazine

Five drops of glacial acetic acid are added at room temperature to a solution of 27.4 g of nicotinyl hydrazide and 28.1 g of 4-chlorobenzaldehyde in 300 ml of ethanol. The suspension that forms in the course of the weakly exothermic reaction is stirred for 2 hours at room temperature. The precipitated product is isolated by filtration, washed with c. 100 ml of ethanol and dried, affording the title compound of formula

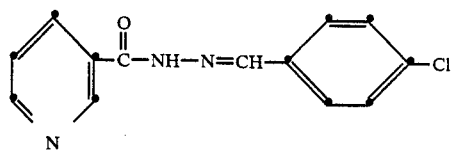

with a melting point of 188°–190° C.

(b) Preparation of 1-chloro-1-pyrid-3-yl)-4-(4-chlorophenyl)-2,3-diazabutadiene (compound 4.2)

A suspension of 44 g of the 1-nicotinoyl-2-(4-chlorobenzylidene) hydrazine obtained in (a) in 700 ml of toluene is heated under reflux. Then 60.5 g of thionyl chloride are added dropwise to this suspension over about 1.5 hours. After 6 hours under reflux, the clear, dark yellow reaction mixture is concentrated by evaporation. The solid residue is suspended in ethyl acetate and the suspension is filtered. The filter residue is dried, affording the title compound of formula

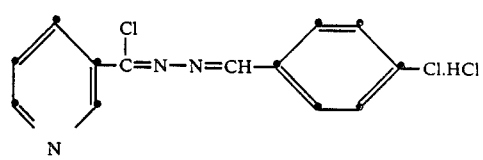

in the form of the hydrochloride with a melting point of 155°–160° C.

(c) Preparation of 2-(pyrid-3-yl)-5-(4-chlorophenyl)-4,5-dihydro-1,3,4-thiadiazole (compound 1.11)

A solution of 13.8 g of potassium hydroxide in 150 ml of ethanol is saturated with hydrogen sulfide. Then 13.8 g of potassium hydroxide in 150 ml of ethanol are added dropwise to this solution. To the resultant solution are added 38.7 g of 1-chloro-1-(pyrid-3-yl)-4-(4-chlorophenyl)-2,4-diazabutadiene hydrochloride (obtained in (b)), in portions, while cooling with ice. The reaction mixture is subsequently stirred for 1 hour at room temperature, then concentrated, and the residue is dissolved in ethyl acetate. The ethyl acetate solution is washed twice with water and twice with a saturated solution of sodium chloride, dried over sodium sulfate, filtered, and concentrated by evaporation, affording the title compound of formula

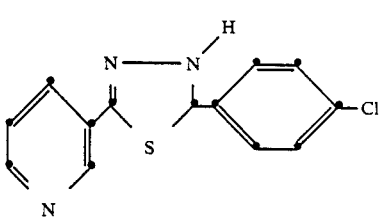

with a melting point of 108°–110° c. (compound 1.11).

The following compounds of formula I and formula IVa can also be prepared in accordance with the foregoing procedures:

Compounds 1.1 to 1.33 of formula I and compounds 4.1 and 4.2 of formula IVa of Tables 1 and 2 can be prepared in accordance with the described procedures.

TABLE 1
Compounds of formula I

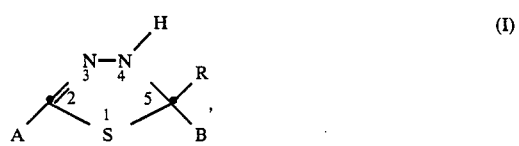

| Compound | A | B | R | Physical data (°C.) |
|---|---|---|---|---|
| 1.1 | pyrid-3-yl | pyrid-3-yl | H— | m.p. 77–78° |
| 1.2 | pyrid-3-yl | pyrid-2-yl | H— | |
| 1.3 | pyrid-3-yl | pyrid-4-yl | H— | |
| 1.4 | pyrid-2-yl | pyrid-2-yl | H— | |
| 1.5 | pyrid-2-yl | pyrid-3-yl | H— | |
| 1.6 | pyrid-2-yl | pyrid-4-yl | H— | |
| 1.7 | pyrid-4-yl | pyrid-2-yl | H— | |
| 1.8 | pyrid-4-yl | pyrid-3-yl | H— | |
| 1.9 | pyrid-4-yl | pyrid-4-yl | H— | |
| 1.10 | pyrid-3-yl | pyrid-3-yl | $CH_3$— | |
| 1.11 | pyrid-3-yl | H | 4-Cl—$C_6H_4$ | m.p. 108–110° |
| 1.12 | pyrid-3-yl | H | H | |
| 1.13 | Pyrid-3-yl | —$CH_3$ | H | |
| 1.14 | pyrid-3-yl | —$CH_3$ | —$CH_3$ | |
| 1.15 | pyrid-3-yl | pyrid-3-yl | H | |
| 1.16 | pyrid-3-yl | pyrid-2-yl | H | |
| 1.17 | pyrid-3-yl | pyrid-4-yl | H | |
| 1.18 | pyrid-3-yl | pyrid-3-yl | $CH_3$ | |
| 1.19 | pyrid-3-yl | H | 3,4-di-Cl-phenyl | m.p. 168–170° |
| 1.20 | pyrid-3-yl | H | 4-$OCH_3$-phenyl | m.p. 79–80° |
| 1.21 | pyrid-3-yl | H | 4-$CF_3$-phenyl | |
| 1.22 | pyrid-3-yl | H | 4-F-phenyl | m.p. 80–82° |
| 1.23 | pyrid-3-yl | H | 4-$CH_3$-phenyl | m.p. 97–98° |
| 1.24 | pyrid-3-yl | H | 3-F-phenyl | m.p. 86–88° |
| 1.25 | pyrid-3-yl | H | 2-Cl-phenyl | m.p. 155–157° |
| 1.26 | pyrid-3-yl | H | 4-$NO_2$-phenyl | |

TABLE 1-continued

Compounds of formula I

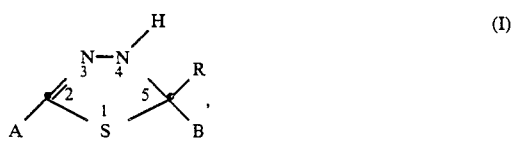

| Compound | A | B | R | Physical data (°C.) |
|---|---|---|---|---|
| 1.27 | pyrid-3-yl | H | —⟨benzene⟩—OCHF₂ | |
| 1.28 | pyrid-2-yl | H | —⟨benzene⟩—Cl | |
| 1.29 | pyrid-2-yl | H | —⟨benzene⟩(Cl)—Cl | |
| 1.30 | pyrid-4-yl | H | —⟨benzene⟩—Cl | |
| 1.31 | pyrid-4-yl | H | —⟨benzene⟩—CF₃ | |
| 1.32 | pyrid-3-yl | pyrid-3-yl | H | oxalate m.p. 143–144° |
| 1.33 | pyrid-4-yl | pyrid-3-yl | H | m.p. 86–88° |

(All R groups for 1.27–1.31 are substituted phenyl as depicted.)

$$\underset{A}{\overset{}{\diagdown}}\!\!\!\underset{2}{\overset{N_3\!-\!N_4\text{-}H}{\diagup}}\!\!\!\underset{S_1}{\ }\!\!\!\underset{5}{\diagdown}\!\!\!\underset{B}{\overset{R}{\diagup}} \quad (I)$$

TABLE 2

Compounds of formula IVa

| Compound | A | B' | R' | Physical data (°C.) |
|---|---|---|---|---|
| 4.1 | pyrid-3-yl | pyrid-3-yl | H | m.p. 103–105° |
| 4.2 | pyrid-3-yl | H | Cl—⟨pyridyl⟩— | m.p. 155–60° (hydrochloride) |
| 4.3 | | | | |
| 4.4 | | | | |

FORMULATION EXAMPLES

Formulations for active ingredients of formula I according to Example 1 or combinations thereof with other insecticides or acaricides (throughout, percentages are by weight)

| 1. Wettable powders | (a) | (b) | (c) |
|---|---|---|---|
| compound of formula I or combination | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether | — | 2% | — |

| -continued | | | |
|---|---|---|---|
| 1. Wettable powders | (a) | (b) | (c) |
| (7–8 moles of ethylene oxide) | | | |
| highly dispersed silicic acid | 5% | 10% | 10% |
| kaolin | 62% | 27% | — |

The active ingredient or combination is thoroughly mixed with the adjuvants and the mixture is thoroughly ground in a suitable mill, affording wettable powders which can be diluted with water to give suspensions of the desired concentration.

| 2. Emulsifiable concentrate | |
|---|---|
| compound of formula I or combination | 10% |
| octylphenol polyethylene glycol ether (4–5 moles of ethylene oxide) | 3% |
| calcium dodecylbenzenesulfonate | 3% |
| castor oil polygycol ether (36 moles of ethylene oxide) | 4% |
| cyclohexanone | 30% |
| xylene mixture | 50% |

Emulsions of any required concentration can be obtained from this concentrate by dilution with water.

| 3. Dusts | (a) | (b) |
|---|---|---|
| compound of formula I or combination | 5% | 8% |
| talcum | 95% | — |
| kaolin | — | 92% |

Ready for use dusts are obtained by mixing the active ingredient with the carrier, and grinding the mixture in a suitable mill.

| 4. Extruder granulate | |
|---|---|
| compound of formula I or combination | 10% |
| sodium lignosulfonate | 2% |
| carboxymethylcellulose | 1% |
| kaolin | 87% |

The active ingredient or combination is mixed and ground with the adjuvants, and the mixture is subsequently moistened with water. The mixture is extruded and then dried in a stream of air.

| 5. Coated granulate | |
|---|---|
| compound of formula I or combination | 3% |
| polyethylene glycol (mol. wt. 200) | 3% |
| kaolin | 94% |

The finely ground active ingredient or combination is uniformly applied, in a mixer, to the kaolin moistened with polyethylene glycol. Non-dusty coated granulates are obtained in this manner.

| 6. Suspension concentrate | |
|---|---|
| compound of formula I or combination | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient or combination is intimately mixed with the adjuvants, giving a suspension concentrate from which suspensions of any desired concentration can be obtained by dilution with water.

BIOLOGICAL EXAMPLES

Example B1

Insecticidal contact action against *Myzus persicae*

Pea seedlings which have been cultivated to a height of about 4 cm in water are each populated with c. 200 aphids of the species *Myzus persicae* before the start of the test. The treated plants are sprayed to drip point 24 hours later with aqueous suspensions containing compound 1.11 in concentrations of 200, 100, 50, 25, 12 and 6 ppm. An evaluation of percentage mortality is made 48 hours after application. The test is carried out at 20°–22° C. and 60% relative humidity.

Result:

| concentration in ppm: | 200 | 100 | 50 | 25 | 12 | 6 |
|---|---|---|---|---|---|---|
| mortality (%) | 100 | 99 | 98 | 97 | 97 | 92 |

Example B2

Action against *Musca domestica*

50 g of freshly prepared CMSA nutrient substrate for maggots are charged into each of a number of beakers. A specific amount of an acetonic solution containing 1% by weight of the respective test compound is pipetted onto the nutrient substrate present in the beakers to give an active ingredient concentration of 800 ppm. The substrate is then thoroughly mixed and the acetone subsequently allowed to evaporate over a period of at least 20 hours.

Then 25 one-day-old maggots of *Musca domestica* are put into each of the beakers containing the treated nutrient substrate for testing with each active ingredient at the given concentration. After the maggots have pupated, the pupae are separated from the substrate by flushing them out with water and then deposited in containers closed with a perforated top.

Each batch of flushed out pupae is counted to determine the toxic effect of the test compound on the maggot development. A count is then made after 10 days of the number of flies which have hatched out of the pupae.

Compounds of formula I according to Table 1 are very effective in this test.

Example B3

Action against *Lucilia sericata*

1 ml of an aqueous formulation containing 0.5% of test compound is added at 50° C. to 9 ml of a culture medium. Then about 30 freshly hatched *Lucilia sericata* larvae are added to the culture medium, and the insecticidal action is determined after 48 and 96 hours by evaluating the mortality rate.

Compounds of formula I according to Table 1 are very effective against *Lucilia sericata* in this test.

Example B4

Action against *Aedes aegypti*

A concentration of 800 ppm is obtained by pipetting a specific amount of a 0.1% solution of the test compound in acetone onto the surface of 150 ml of water in a beaker. After the acetone has evaporated, 30 to 40 two-day old larvae of *Aedes aegypti* are put into the beaker containing the test compound. Mortality counts are made after 2 and 7 days.

Compounds of formula I according to Table 1 are very effective in this test.

Example B5

Contact action against *Aphis craccivora*

Before the start of the test, 4- to 5-day old bean seedlings (*Vicia faba*) reared in pots are each populated with about 200 insects of the species *Aphis craccivora*. The treated plants are sprayed direct to drip point 24 hours later with an aqueous formulation containing 12.5 ppm of the test compound. Two plants are used for each test compound at its given concentration. A mortality count is made after 24 and 72 hours respectively. The test is carried out at 21°–22° C. and at a relative humidity of about 55%.

In this test, compound 1.11 of Table 1 effects 80 to 100% kill.

Example B6

Systemic action against *Myzus persicae* (in water)

Pea seedlings (2 cm in height) which have been populated before the start of the test with c. 200 aphids of the species *Myzus persicae* (R-strain) are placed into 20 ml of an aqueous spray mixture containing 100 ppm of the test compound. The spray mixture is prepared by diluting an emulsifiable concentrate or a wettable powder with water. The roots of the pea plantlets are pushed through a centre hole in the plastic top of the test tube containing the spray mixture. The test is carried out at 21° C. and 60% relative humidity. After 2, 3 and 6 days a percentage evaluation is made of aphids which are no longer capable of sucking in order to establish whether the test compound absorbed through the roots is able to kill the insects present on the upper parts of the plants.

The mortality count is made 48 and 72 hours after the start of the test. Two plants, each in a separate pot, are used for each test compound. The test is carried out at 25° C. and c. 75% relative humidity.

Compounds of formula I according to Table 1 are very effective in this test.

Example B7

Systemic action against *Myzus persicae*

Pimenta plants in the 4- to 5-leaf stage, in pots containing 600 ccm of soil, are populated with 200–400 aphids of the species *Myzus persicae*. Then 50 ml of an aqueous formulation (prepared from a 25% wettable powder) or emulsifiable concentrate of the test compound are poured in a concentration of 400 ppm direct on to the soil without wetting the plants themselves. A mortality count is made 3 and 6 days after treatment.

Two plants are used for each test compound. The test is carried out at c. 22° C. and 60% relative humidity.

Compounds of formula I according to Table 1 are very effective in this test.

Example B8

Leaf penetration action against *Aphis craccivora*

A small shoot of *Vicia faba*, which is highly infested with aphids of the species *Aphis craccivora*, is placed in each of a number of 8 cm high plastic beakers (diameter about 6 cm). Each beaker is covered with a cardboard lid having a punched opening of 2.5 cm diameter in the centre. A leaf of a *Vicia faba*-plant is then placed over the opening in the lid without separating this leaf from the potted plant. The leaf is then fixed on the beaker with a second punched cardboard lid above the opening of the first lid. From underneath, i.e. through the opening of the first lid, the aphids in the beaker then infect the leaf of the plant used as bait. An aqueous formulation of the test compound is then applied in a concentration of 800 ppm uniformly with a brush to the top side of the leaf. An investigation is then made to determine whether the test substance applied to the top side of the leaf of the plant used as bait has diffused in sufficient amount through the leaf to its underside to kill aphids sucking thereon.

The test is carried out at about 20° C. and 60% relative humidity. The evaluation of percentage mortality is made 48 hours after application of the test compound.

Compounds of formula I according to Table 1 are very effective in this test.

Example B9

Action against *Laodelphax striatellus* and *Nilaparvata lugens* (nymphs)

The test is carried out with growing plants. For this purpose 4 rice plants (thickness of stem 8 mm) about 20 cm in height are planted into each of a number of pots (diameter 8 cm). The plants in each pot are sprayed on a rotary table with 100 ml of an acetonic solution containing 400 ppm of the respective test compound. After the spray coating has dried, each plant is populated with 20 nymphs of the test organisms in the third stage. To prevent the cicadas from escaping, a glass cylinder open at both ends is slipped over each of the plants and sealed with a gauze top. The nymphs are kept for 10 days on the treated plant until the next development stage has been reached. Evaluation of percentage mortality is made 1, 4 and 8 days after treatment.

Compounds of formula I according to Table 1 are very effective in this test.

Example B10

Ovicidal action against *Laodelphax striatellus* and *Nilaparvata lugens*

The test ist carried out with growing plants. For this purpose 4 rice plants (thickness of stem 8 mm; height about 20 cm) are planted into each of a number of pots (diameter 8 cm).

The plants in each pot are sprayed on a rotary table with 100 ml of an acetonic solution containing 400 ppm of the respective test compound. After the spray coating has dried, each plant is populated with 3 adult females. To prevent the females from escaping, a glass cylinder is slipped over each of the plants and sealed with a gauze top. The females are left on the treated plant for 4 days for oviposition and are then removed.

About 8 days after the females have been placed on the plants, the young cicadas hatch from the eggs and a count is made. The percentage mortality is calculated by comparing the number of larvae which have hatched on the treated plants with the number which have hatched on the untreated control plants.

Compounds of formula I according to Table 1 are very effective in this test.

What is claimed is:

1. A 2-pyridyl-4,5-dihydro-1,3,4-thiadiazole of formula I

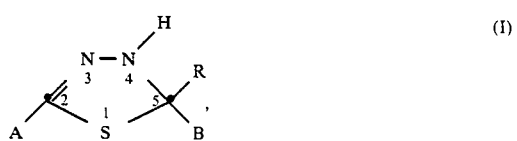

wherein
A is the 2-, 3- or 4-pyridyl radical,
B is hydrogen, $C_1$–$C_4$alkyl or the 2, 3- or 4-pyridyl radical,
R is hydrogen, $C_1$–$C_4$alkyl, benzyl or 1- or 2-naphthyl which is unsubstituted or substituted by halogen, nitro, $C_1$–$C_4$alkyl, $C_1$–$C_4$alkoxy, $C_1$–$C_4$alkoxy-$C_1$–$C_4$-alkyl or halo-$C_1$–$C_4$alkyl.

2. A compound according to claim 1, wherein B is the 2-, 3- or 4-pyridyl radical and R is hydrogen or $C_1$–$C_4$alkyl.

3. A compound according to claim 2, wherein A is the 2-pyridyl radical and R is hydrogen.

4. A compound according to claim 2, wherein A is the 2-pyridyl radical and R is hydrogen.

5. 2,5-Bis(3-pyridyl)-4,5-dihydro-1,3,4-thiadiazole or a salt thereof according to claim 4.

6. A compound according to claim 2, wherein A is the 4-pyridyl radical and R is hydrogen.

7. A pesticidal composition which contains, as active component, a pesticidally active amount of a compound as claimed in claim 1 together with suitable carriers and/or other adjuvants.

8. A method of controlling insects and representatives of the order Acarina, which comprises treating or contacting said pests, their various development stages or the locus thereof, with a pesticidally effective amount of a compound of formula I according to claim 1 or with a composition which contains a pesticidally effective amount of such a compound, together with adjuvants and carriers suitable therefor.

9. A method according to claim 8 for controlling insects and representatives of the order Acarina that are pests of animals and plants.

10. A method according to claim 9 for controlling plant-destructive insects.

11. A method according to claim 10 for controlling plant-destructive sucking insects.

* * * * *